United States Patent
Tapper et al.

(10) Patent No.: US 10,806,211 B1
(45) Date of Patent: Oct. 20, 2020

(54) FOOTWEAR HAVING THERAPEUTIC LIGHT SOURCE

(71) Applicant: Biothread LLC, Wayne, PA (US)

(72) Inventors: Jay Tapper, Wayne, PA (US); Jens Johnson, Austin, TX (US); Lawrence A. Blaustein, Chagrin Falls, OH (US); Jaleh Factor, Manhattan Beach, CA (US); Charles Peter Althoff, Piermont, NY (US); Lulin Ding, Brooklyn, NY (US); Boris Kontorovich, Brooklyn, NY (US); Kevin T. Foley, Germantown, TN (US)

(73) Assignee: Biothread LLC, Wayne, PA (US)

( * ) Notice: Subject to any disclaimer, the term of this patent is extended or adjusted under 35 U.S.C. 154(b) by 0 days.

(21) Appl. No.: 16/520,885

(22) Filed: Jul. 24, 2019

(51) Int. Cl.
*A43B 3/00* (2006.01)
*A43B 23/02* (2006.01)
*A61N 5/06* (2006.01)

(52) U.S. Cl.
CPC ............ *A43B 3/001* (2013.01); *A43B 23/025* (2013.01); *A61N 5/0622* (2013.01); *A61N 2005/063* (2013.01); *A61N 2005/0645* (2013.01)

(58) Field of Classification Search
CPC .... A61N 5/06–2005/073; A61B 18/20–18/28; A43B 3/00–3/001; A43B 23/00–23/06
See application file for complete search history.

(56) References Cited

U.S. PATENT DOCUMENTS

| | | | |
|---|---|---|---|
| 4,885,663 A * | 12/1989 | Parker | G02B 6/001 362/561 |
| 5,813,148 A | 9/1998 | Guerra | |
| 8,585,707 B2 * | 11/2013 | Rogers | A61N 5/062 606/88 |
| 8,621,891 B2 | 1/2014 | Dua | |
| 9,549,585 B2 * | 1/2017 | Amos | G01L 1/22 |
| 9,687,577 B2 * | 6/2017 | Dobrinsky | A61L 2/10 |
| 2006/0221596 A1 | 10/2006 | Chang | |
| 2007/0288071 A1 * | 12/2007 | Rogers | A61N 5/062 607/88 |
| 2008/0308748 A1 * | 12/2008 | Burrows | A43B 1/0036 250/491.1 |
| 2009/0034236 A1 | 2/2009 | Reuben | |
| 2012/0291564 A1 * | 11/2012 | Amos | A61B 5/6807 73/862.045 |
| 2016/0074547 A1 * | 3/2016 | Dobrinsky | A61L 2/10 250/492.1 |
| 2019/0133241 A1 | 5/2019 | Chou | |

* cited by examiner

*Primary Examiner* — Jonathan T Kuo
(74) *Attorney, Agent, or Firm* — Rankin, Hill & Clark LLP

(57) ABSTRACT

An article of footwear is configured to be worn so as to at least partially cover a wearer's foot. The footwear includes at least one optical fiber on an internal surface of the footwear. The at least one optical fiber is configured to project radiation having a therapeutic wavelength through the at least one optical fiber and toward at least one of the wearer's foot, ankle or leg when the footwear is being worn so as to at least partially cover the wearer's foot.

17 Claims, 12 Drawing Sheets

FOOTWEAR HAVING THERAPEUTIC LIGHT SOURCE

BACKGROUND

US 2006/0221596 discloses an emitting light device for shoes, which purportedly had a capacity for illuminating a larger illuminated area with a preferred effect of light and saving electrical power.

2019/0133241 discloses a light-emitting shoe including a shoe body and a light source. The shoe body includes an upper and a shoe sole mounted to the bottom side of the upper. The upper is made up of a woven fabric composed of a plurality of warp yarns, a plurality of weft yarns and a plurality of fiber optic yarns. The light source is mounted in an accommodation chamber in the shoe sole and connects to one end of each fiber optic yarn for emitting light into the fiber optic yarns so that the emitted light of the light source is evenly distributed throughout the upper of the shoe body via the fiber optic yarns.

U.S. Pat. No. 5,813,148 discloses footwear having optical fiber illuminating display areas that provides emphasis on illuminating certain features of the footwear, such as trademarks, logos, team sports, cartoon characters, and other artistic designs primarily for advertising, decoration and enhancing the visibility of the wearer.

The aforementioned patent documents are concerned with directing light outward to produce a warning effect or enhance the outward visual effect of the shoe. Also, typically shoes include a fabric inner liner, which would inhibit light emanating outwards from coming into contact with the wearer's foot for the shoes in the aforementioned patent documents.

US 2009/0034236 discloses a shoe with ultraviolet LEDs embedded in a UV transmissive photocatalyst coated sole or positioned inside the upper to irradiate photocatalyst coated surfaces. Electrons released by the photocatalyst or the surface recombination purportedly have efficacy in surface sanitization or in odor control. This patents mentions that a foot presence sensor may be utilized since direct exposure of the foot to UV may be undesirable, which indicates that the LEDs are intended to be illuminated when the shoe is not being worn.

U.S. Pat. No. 8,621,891 discloses an article footwear having an upper that includes a knit element. Inlaid strands extend through the knit element and may provide support, stability, and structure to the knit element. The inlaid strands may assist with securing the upper around the foot, limit deformation in areas of the upper and operate in connection with shoe laces to enhance the fit of the footwear.

SUMMARY

In view of the foregoing, article of footwear is configured to be worn so as to at least partially cover a wearer's foot. The footwear includes at least one optical fiber on an internal surface of the footwear. The at least one optical fiber is configured to project radiation having a therapeutic wavelength through the at least one optical fiber and toward at least one of the wearer's foot, ankle or leg when the footwear is being worn so as to at least partially cover the wearer's foot.

DETAILED DESCRIPTION

An article of footwear 20 (hereinafter referred to simply as "footwear") is depicted in FIG. 1 as including a sole structure 22 and an upper 24. The footwear 20 operates as a light (or radiation) delivery system in that it is configured to project light (or radiation) toward the foot, ankle and/or leg of the wearer. Light having a wavelength between 630 nm and 900 nm has been found beneficial to increase blood flow, may provide ameliorative effects with regard to inflammation, and can be beneficial in the treatment of diabetic neuropathy, and as such can be referred to as light having a therapeutic wavelength. The footwear 20 may be configured, however, to project light at wavelengths other than between 630 nm and 900 nm, which also may have a therapeutic effect.

Figure 1A:
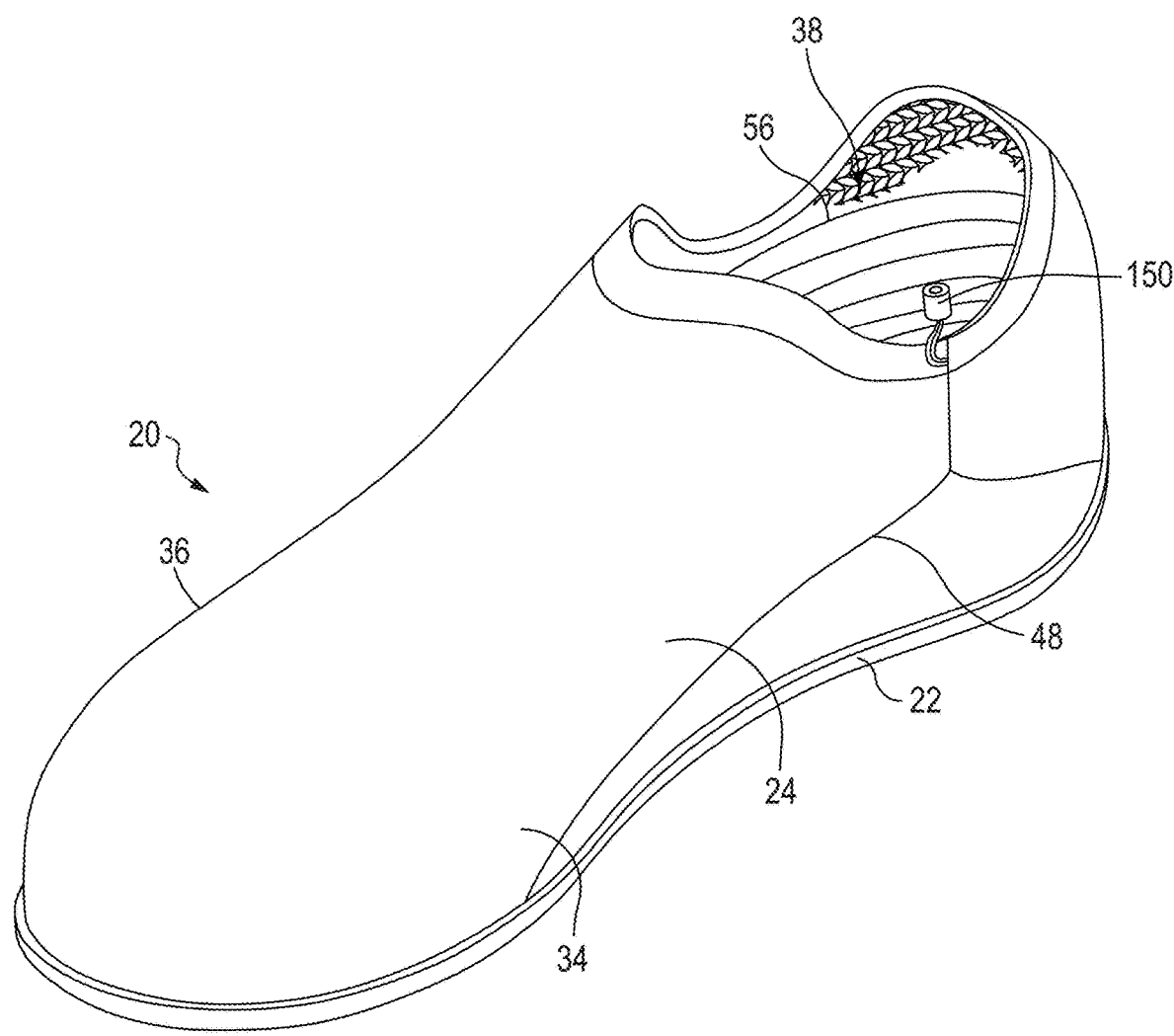
FIGS. 1A-1C are each a perspective view of an article of footwear including a system for providing radiation to a wearer's foot.
Figure 1B:
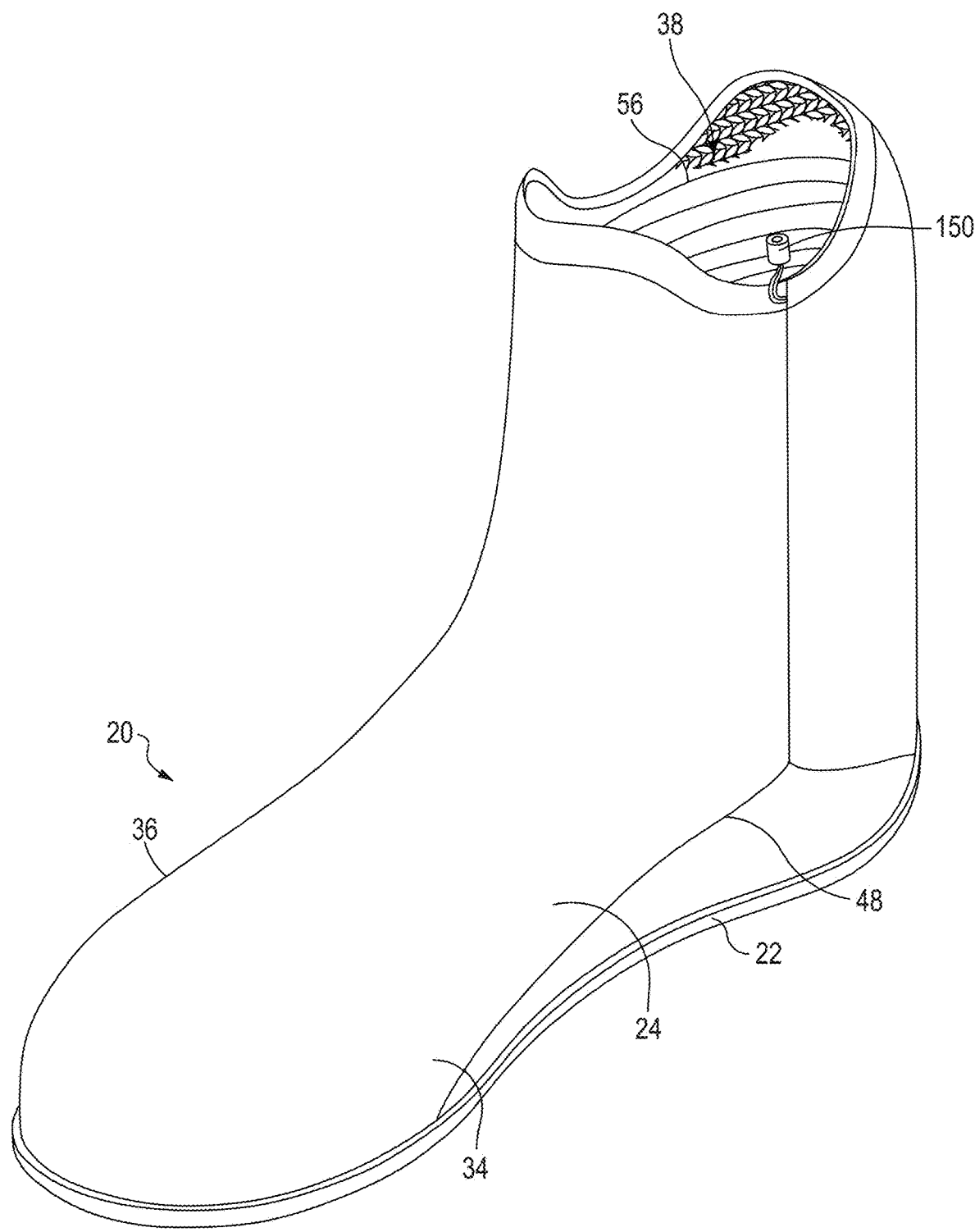
Figure 1C:
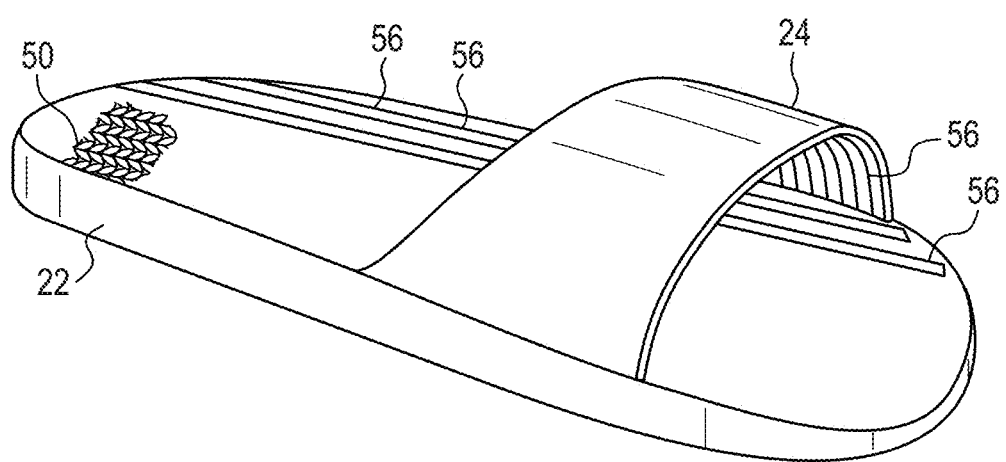

Although the footwear 20 in FIG. 1A is illustrated as having a general configuration suitable for walking, concepts associated with the footwear 20 may also be applied to a variety of other types of footwear, including baseball shoes, basketball shoes, cycling shoes (FIG. 1B), football shoes, tennis shoes, soccer shoes, training shoes, running shoes, and boots, for example. The concepts may also be applied to types of footwear that are generally considered to be non-athletic, including dress shoes, loafers, flip flops, moccasins, clogs, sandals and slides (FIG. 1C). Accordingly, the concepts disclosed with respect to the footwear 20 apply to a wide variety of types of footwear.

Figure 2:
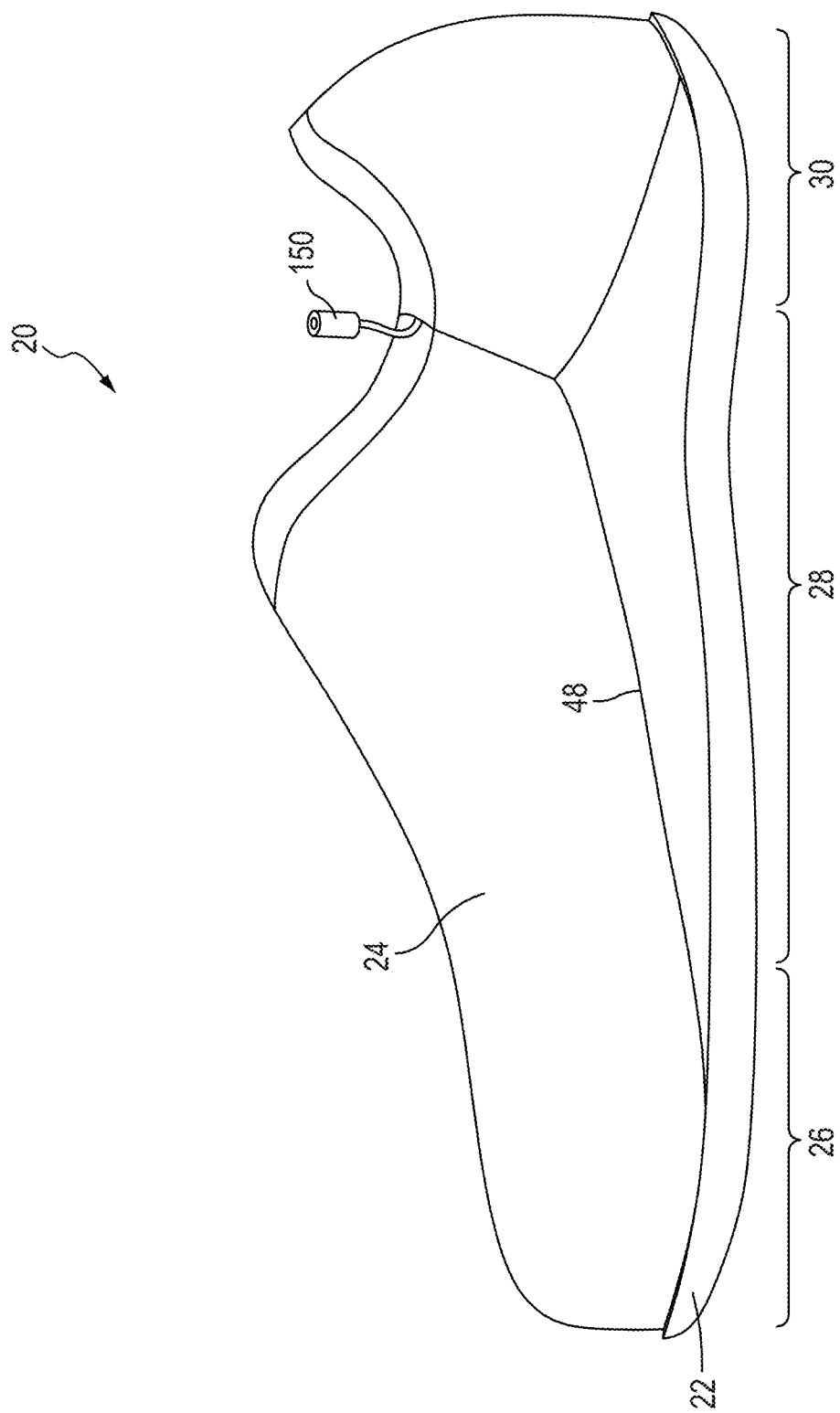
FIG. 2 is a lateral side elevational view of the article of footwear depicted in FIG. 1A.

With reference to FIG. 2, the footwear 20 can be referred to as having three general regions: a forefoot region 26, a midfoot region 28, and a heel region 30. The forefoot region 26 generally includes portions of the footwear 20 receiving the toes and joints connecting the metatarsals with the phalanges of the wearer. The midfoot region 28 generally includes portions of the footwear 20 receiving the arch area of the foot. The heel region 30 generally receives rear portions of the foot, including the calcaneus bone. With reference back to FIG. 1A, the footwear 20 also includes a lateral side 34 and a medial side 36, which extend through each of the forefoot region 26, the midfoot region 28, and the heel region 30. The lateral side 34 corresponds with an outside area of the foot, and the medial side 36 corresponds with an inside area of the foot. The regions 26, 28 and 30 and the sides 34 and 36 are not intended to demarcate precise areas of the footwear 20. Instead, the regions 26, 28 and 30 and the sides 34 and 36 are intended to represent general areas of the footwear 20 and may be applied to the sole structure 22, the upper 24, and individual elements of the footwear 20.

The sole structure 22 is secured to the upper 24 and extends between the foot and the ground when the footwear 20 is worn. The sole structure 22 can include compressible or resilient elements that attenuate ground reaction forces when compressed between the foot and the ground during walking, running, or the like. The sole structure 22 can include a midsole, an outsole and a sockliner similar to conventional sole structures. Although such a configuration for the sole structure 22 provides an example of a sole structure that may be used in connection with the upper 24, a variety of other conventional or nonconventional configurations for the sole structure 22 may also be utilized.

The upper 24 defines a void within footwear 20 for receiving and securing a foot relative to the sole structure 22. In the embodiment illustrated in FIGS. 1A and 1B, the void is shaped to accommodate the foot and extends along a lateral side of the foot, along a medial side of the foot, over the foot, around the heel, and under the foot. In the embodiment illustrated in FIG. 1B, the upper 24 also covers the wearer's ankle and a portion of the lower leg. Access to the void is provided by an opening 38 located in the heel region 30. In other configurations, the footwear 20 may include laces (not shown) extending through lace apertures (not shown) in the upper 24. If desired, the upper 24 may include a tongue. In further configurations, the upper 24 may take other configurations such as including a strap or straps similar to a conventional sandal, flip flop, a slide (FIG. 1C) or even another shoe configuration.

Figure 3:
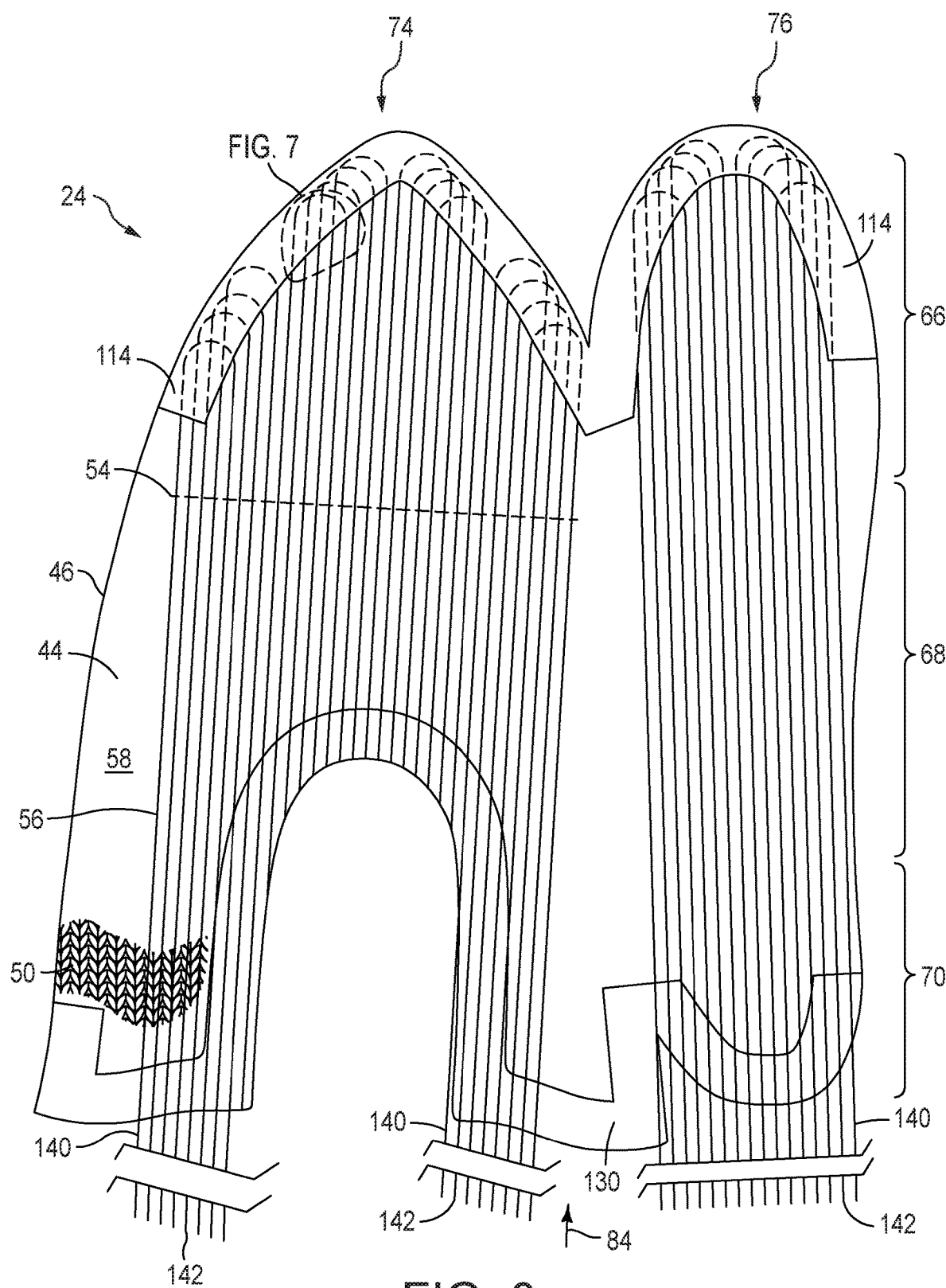
FIG. 3 is a plan view showing an internal surface of a knit element that forms an upper of the article of footwear.

FIG. 3 depicts the upper 24 shown in FIG. 1A separate from the sole structure 22. As illustrated in FIG. 3, the upper 24 is shown as a knit element 44 formed of a unitary knit construction in which the upper 24 is formed as a one-piece knitted element through a knitting process, and the knitting process substantially forms the various features and structures of the upper 24 without the need for significant additional manufacturing steps or processes. Although portions of knit element 44 may be later joined to each other, e.g., sections of a peripheral edge 46 of the knit element 44 can be sewn to other sections of the peripheral edge 46 following the knitting process to provide a seam 48 visible in FIGS. 1A and 2, the knit element 44 remains formed of unitary knit construction because it is formed as a one-piece knit element in a particular pattern suitable to be made into the upper 24 with a limited amount of further manufacturing after the knitting process.

Figure 4:
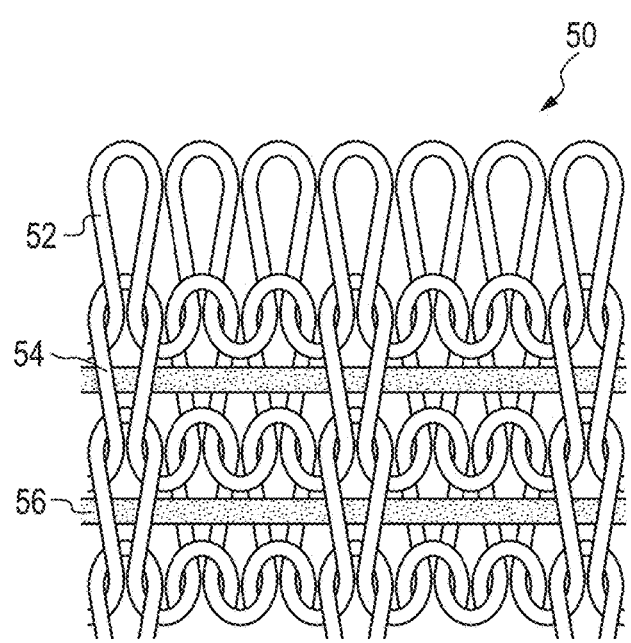
FIG. 4 is a schematic depiction of a knit pattern for the knit element depicted in FIG. 3.
Figure 5:
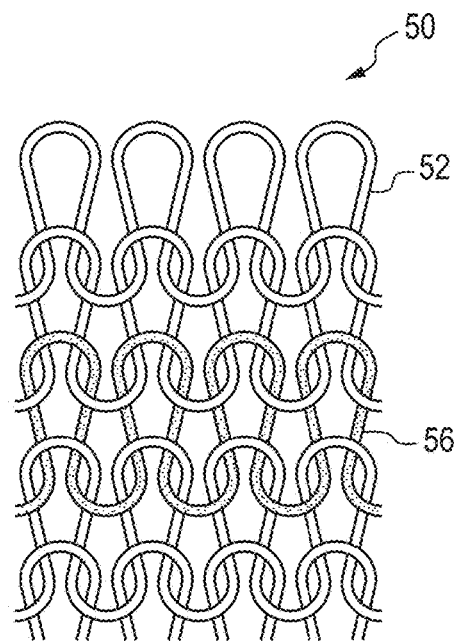
FIG. 5 is a schematic depiction of another knit pattern for a knit element similar to the knit element depicted in FIG. 3.

The knit element 44 in FIG. 3 includes a knitted base layer 50 (only a portion of a knit pattern being depicted in FIG. 3 for clarity purposes) formed from at least one yarn 52 (FIG. 4) having knitted looped threads forming loops 54 (only one line of which being schematically depicted in FIG. 3 for clarity purposes) that hold in position at least one side-emitting optical fiber 56 (hereinafter "optical fiber"), which is laid into the knitted base layer 50 during the same knitting cycle as the knitted base layer 50. The knitted base layer 50 is formed from the at least one yarn 52 that is manipulated (e.g., with a knitting machine) to form a plurality of intermeshed loops that define a variety of courses and wales. That is, the knitted base layer 50 has the structure of a knit textile, and the yarn 52 from which it is made can be a comfortable yarn such as cotton, polyester, cotton/polyester blends, microdenier polyester/cotton blends, wool, nylon, rayon, modal, bamboo and combinations thereof. Such a construction can provide the footwear 20 a comfortable, cozy, cushy, easy to put on/secure, snug, and/or soft feel on the foot of the wearer, especially a wearer who is not wearing socks. It can be desirable to provide a skin-tight form-fitting article of footwear 20 to bring the therapeutic light source, which will be described in more detail below, very close to the wearer of the footwear 20. Accordingly, the yarn 52 from which the knitted base layer 50 is constructed can also include an elastic fiber such as those available under the mark Lycra® or spandex, and more than one type of yarn can form the knitted base layer 50. FIG. 5 depicts an alternative knit construction in which the optical fiber 56 is incorporated as of one of the "yarns" to form one of the courses of the knitted base layer 50. The optical fiber 56 course can be repeated to provide a plurality of optical fiber 56 courses. The knitted base layer 50 can have 100% or nearly 100% recovery in two mutually perpendicular directions from 8% stretch in either direction. This can be desirable when the footwear 20 is in the form of a shoe shown in FIG. 1. Knit fabrics can exhibit mechanical four way stretch, even without the use of elastic fibers, because of the manner in which the fabric is formed. Woven fabrics, in contrast, are typically not four way stretch fabrics, but instead stretch, if at all, along the bias, which is 45 degrees from the warp and weft yarns. Because woven fabrics typically do not stretch, fiber optic threads, which are not resilient, have been woven into fabrics in the weft, or filling direction.

Figure 6:
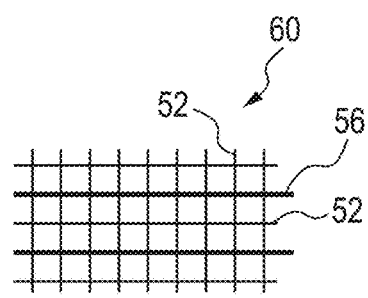
FIG. 6 is a schematic depiction of a woven pattern for a woven element, which can be used in addition to or in lieu of the knit element depicted in FIG. 3

FIG. 6 depicts a fabric base layer as a woven fabric base layer 60 in which the optical fiber 56 is integrated as a yarn in the filling direction; however, if desired the optical fiber 56 can be integrated as a yarn in the warp direction. Accordingly, the upper 24 can be formed from a fabric element that can include the knit element 44, a woven element similar to that shown in FIG. 6 or another type of fabric element, e.g., a non-woven fabric.

With reference back to FIG. 3, the optical fiber 56 is an inlaid fiber provided on an internal surface 58 of the knit element 44 that extends through the knit element 44 and passes between the various loops 54 within the knitted base layer 50. An outer diameter of each optical fiber 56 can be between about 0.25 mm and about 0.75 mm, which is typically larger than an outer diameter of the yarn 52 from which the knitted base layer 50 is knitted. Although the optical fiber 56 generally extends along courses within knit element 44, the optical fiber 56 may also extend along wales within knit element 44. Not only does the optical fiber 56 provide therapeutic light to the wearer of the footwear 20, which will be described in further detail below, but the optical fiber 56 may also provide structural integrity to the upper 24 so as to provide support, stability, and structure to the upper 24. For example, the optical fiber 56 may limit deformation in areas of upper 24 by imparting stretch-resistance, for example, and/or the optical fiber 56 is configured to accommodate a tensile force so as to provide structural integrity to the upper 24.

Unlike the footwear described above in the background section, the footwear 20 is configured to project light, which can have a therapeutic wavelength, toward (as opposed to away from) a targeted body area of a person wearing the footwear 20. The targeted body areas can include muscle, muscle groups, joints and human extremities, as examples. The footwear 20 in FIGS. 1A-1C are designed to be worn by a person in a similar manner as a conventional shoe, boot or slide so as to direct light toward the foot, ankle and/or leg of the wearer. As mentioned above, the footwear 20 shown in FIGS. 1A-1C are only examples, and the footwear 20 can take other configurations such as baseball shoes, basketball shoes, cycling shoes, football shoes, tennis shoes, soccer shoes, training shoes, running shoes, hiking boots, dress shoes, loafers, sandals, flip flops, moccasins and work boots.

With reference to FIG. 3, the knit element 44 is shown in plan view with the internal surface 58 exposed. As mentioned above, the knit element 44 is formed as a one-piece knitted element through a knitting process, which substantially forms the various features and structures of the upper 24 without the need for significant additional manufacturing steps or processes. The knitting process from which the knit element 44 is manufactured can provide a feature-rich process that automatically integrates the optical fiber 56 into the knit element 44 as opposed to being applied afterwards to the upper 24. By utilizing such a feature-rich knitting process to integrate the optical fiber 56 into the knit element 44, the optical fiber 56 can be cut nearly anywhere along its length and need not exit the knit element along the selvages of the knit element 44, which often is not the case when using a woven fabric in which optical fibers are woven with conventional yarns.

FIG. 3 depicts the optical fiber 56 as an inlaid fiber provided on the internal surface 58 of the knit element 44. In an alternative manner, the optical fiber 56 can be embroidered to the internal surface 58. In contrast to conventional embroidery, which is used to decorate the visible surfaces of fabric garments, in this instance a thread, which can take the place of the loops 54 within the knitted base layer 50, can be used to retain the optical fiber 56 to the internal surface of the knit element 44. Also, if a woven element (see FIG. 6) or another fabric element is used as part of the upper 24, for example, the optical fiber 56 could also be embroidered to that fabric element. The thread, which can take the place of the loops 54 shown in FIG. 3, can be transparent to allow light to travel through it. Also, by employing an embroidering process to retain the optical fiber 56 to the internal surface 58 of the knit element 44 more options as to the layout of the optical fibers 56 may be more available. For example, the majority of the length of each optical fiber 56 shown in FIG. 3 runs perpendicular to the direction that the knit element 44 comes off the knitting machine from which the knit element 44 is made. Since the embroidering process would be used to affix the optical fiber 56 to the knit element 44 after the knit element 44 has been made (albeit without the inlaid optical fiber 56 shown in FIG. 3), the optical fiber 56 could be laid out in nearly any configuration and not be limited to running perpendicular to the direction that the knit element 44 comes off the knitting machine.

The knit element 44 (or other fabric element) and the later formed upper 24 can include a forefoot area 66, which coincides with the forefoot region 26, a midfoot area 68, which coincides with the midfoot region 28, and a heel area 70, which coincides with the heel region 30. The optical fiber 56 can be located in each of the forefoot area 66, the midfoot area 68, and the heel area 70. The knit element 44 (or other fabric element) can also include a top portion 74, which covers the top, medial and lateral sides of the wearer's foot, and a bottom portion 76 that extends along the bottom, or sole, of the wearer's foot.

Unlike typical optical fibers, such as an optical fiber used to transmit light between two ends of the optical fiber in fiber-optic communications, at least within light-emitting zones of the upper 24, the optical fiber 56 transmits light outwardly, e.g. 360 degrees around an axis aligned along a length of the side-emitting optical fiber, along a portion of or the entire length of the optical fiber 56. Also, the optical fiber 56 is configured to project radiation having a therapeutic wavelength through the optical fiber and toward the wearer's foot, ankle and/or leg when the footwear is being worn so as to at least partially cover the wearer's foot, ankle and/or leg. Even though some light may radiate outward, a substantial portion of radiation output from the optical fibers 56 is directed toward the wearer's foot when the footwear is being worn.

The optical fiber 56 can be one having a core made from a material, e.g., polymethyl methacrylate, having a high refractive index surrounded by a cladding, which can be a fluorinated polymer. The light escapes through the cladding to allow the optical fiber 56 to emit light, preferably 360 degrees around an axis, along its length. It is known to provide notches or scratches in cladding to allow light to escape. For example, U.S. Pat. No. 4,234,907 discloses using a cylindrical cutter rolled over the optical fibers to cut notches therein. In contrast, in the illustrated embodiment, the optical fibers 56 can be twisted prior to be inlaid into the knit element 44. This twisting of the optical fibers 56 breaks the cladding to allow more light to escape along the length of the optical fiber 56. In addition to, or in lieu or twisting the optical fibers 56, the optical fibers 56 can be stretched, e.g. pulled, prior to the knitting process and/or during the knitting process. Stretching the optical fibers 56 can also break the cladding to allow more light to escape along the length of the optical fiber 56. Also, the optical fibers 56 can be twisted and stretched during the knitting process of the knit element 44.

In contrast to providing discrete LEDs, for example, embedded in the upper 24 in each of the light-emitting zones, which can result in an article of footwear that can be uncomfortable to wear, a light source 80 (FIG. 10) or multiple light sources can be remote and the optical fiber 56 can transmit the light from the light source 80 to light-emitting zones of the upper 24. Examples of such light-emitting zones will be described with reference to FIG. 3. Each or only some of the light emitting zones may be provided in the upper 24. The knit element 44 (or other fabric element) is configured such that when assembled into the upper 24, the optical fiber 56 is located in the forefoot area 66 of the upper 24 so as to project light toward toes of the wearer of the footwear 20. Since the optical fiber 56 is provided on both the top portion 74 and the bottom portion 76 of the knit element 44 (or other fabric element), when assembled into the upper 24, the optical fiber 56 is located so as to project light toward the underside and the top of the toes of the wearer of the footwear 20. Similarly, the knit element 44 (or other fabric element) is configured such that when assembled into the upper 24, the optical fiber 56 is located in the midfoot area 68 of the upper 24 so as to project light toward an area of the foot between the toes and heel of the wearer of the footwear 20. Because the optical fiber 56 is provided on both the top portion 74 and the bottom portion 76 of the knit element 44 (or other fabric element), when assembled into the upper 24, the optical fiber 56 is located so as to project light toward the underside and the top of an area of the foot between the toes and heel of the wearer of the footwear 20. Moreover, the optical fiber 56 is located so as to project light toward at least one, and in the depicted embodiment both, of the lateral side and a medial side of the foot of the wearer of the footwear 20. In addition, the knit element 44 (or other fabric element) is configured such that when assembled into the upper 24, the optical fiber 56 is located in the heel area 70 of the upper 24 so as to project light toward the heel and ankle of the foot of the wearer of the footwear 20. When assembled into the upper 24, the optical fiber 56 can be located so as to project light toward the underside (sole) and sides of heel of the wearer of the footwear 20. Accordingly, the optical fiber 56 can be located in the upper 24 so as to project light toward a top, a bottom, a lateral side and a medial side of the foot of the wearer of the footwear 20.

In the illustrated embodiment, each optical fiber 56 is aligned substantially parallel to a direction of donning (see arrow 84) of the footwear 20 along at least a majority of a length of each respective optical fiber 56. The footwear 20 is pulled in the direction of donning (arrow 84) when being put on by the wearer, and the direction of donning in the illustrated embodiment is perpendicular to the direction that the knit element 44 comes off of the knitting machine. More particularly, each optical fiber 56 within the top portion 74 and the bottom portion 76 is aligned substantially parallel to the direction of donning (arrow 84). Such an orientation of the optical fibers 56 facilitates donning of the footwear 20 while inhibiting accidental snagging of the optical fibers 56 while the footwear 20 is being donned.

Figure 7:
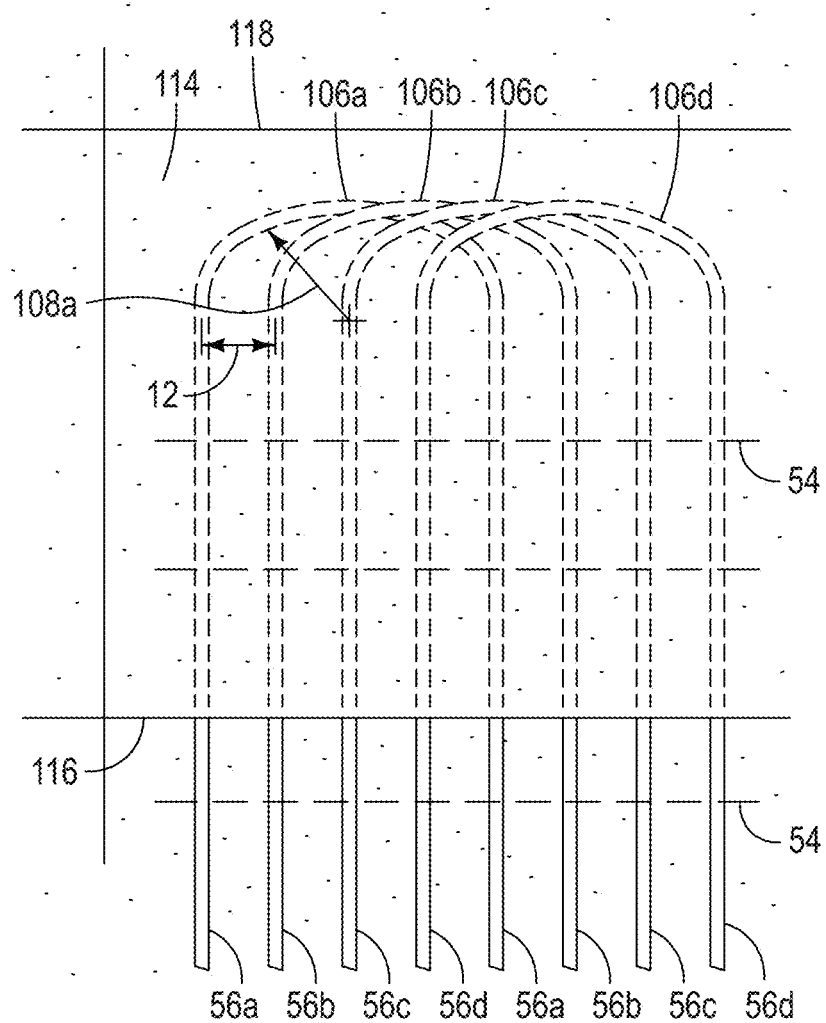
FIG. 7 is close-up view of a portion of FIG. 3.

FIG. 7 depicts a close-up view of the top portion 74 in the forefoot area 66 of the upper 24, which covers the toenails of the wearer of the footwear 20 when worn. The bottom portion 76 in the forefoot area 66, which is visible in FIG. 3 and covers the lower surface of the wearer's toes, has a similar construction. Each optical fiber 56a, 56b, 56c, 56d includes a respective loop 106a, 106b, 106c, 106d positioned within the forefoot area 66 of the footwear 20. Each loop 106a, 106b, 106c, 106d has a radius (only radius 108a is shown in FIG. 7 for purposes of clarity) that is greater than spacing 112 (only spacing between optical fibers 56a and 56b is shown in FIG. 7 for purposes of clarity) between adjacent optical fibers along portions of the respective optical fibers aligned substantially parallel to a direction of donning of the footwear 20. In the illustrated embodiment, the radius 108a is greater than the spacing 112 between adjacent optical fibers 56 along portions of the respective optical fibers located within the top portion 74 and the bottom portion 76 of the upper 24. This results in the optical fibers 56a, 56b, 56c, 56d being "cascaded" in that the first optical fiber 56a crosses over optical fibers 56b, 56c, and 56d. Similarly, the second optical fiber 56b crosses over optical fibers 56a, 56c, and 56d, and so on.

The knitted loops 54 hold the side-emitting optical fibers 56 in position so as to maintain the desired spacing 112, which can be less than about 6.35 mm. The knitted loops 54, however, need not preclude movement of the respective side-emitting optical fibers 56 with respect to the knitted base layer 50 in the direction of donning (arrow 84 in FIG. 3), e.g., along the length of the optical fibers 56.

The forefoot area 66 is constructed so as to include a double layer construction. Each loop 106a, 106b, 106c and 106d is positioned between opposing layers of the double layer construction so that a toe tunnel 114 is provided in the forefoot area 66. The double layer construction in the forefoot area 66 is open at an edge 116 nearer to the midfoot area 68 to receive the plurality of side-emitting optical fibers 56 between the opposing layers. A distal seam 118 is provided where the opposing layers of the double layer construction are connected. The distal seam 118 can limit movement of the optical fibers 56 with respect to the knitted base layer 50. For example, if one end of the first optical fiber 56a is pushed in a direction opposite that of the direction of donning (arrow 84 in FIG. 3), the loop 106a would want to travel toward the distal seam 118. This is because the knitted loops 54 hold the optical fibers 56 in position so as to maintain the desired spacing 112, and do not preclude movement of the respective optical fibers 56 with respect to the knitted base layer 50 in a direction parallel to the direction of donning (arrow 84 in FIG. 3). If the loop 106a were to come into contact with the distal seam 118, further travel of the first optical fiber 56a parallel to and opposite that of the direction of donning would be precluded.

Figure 8:
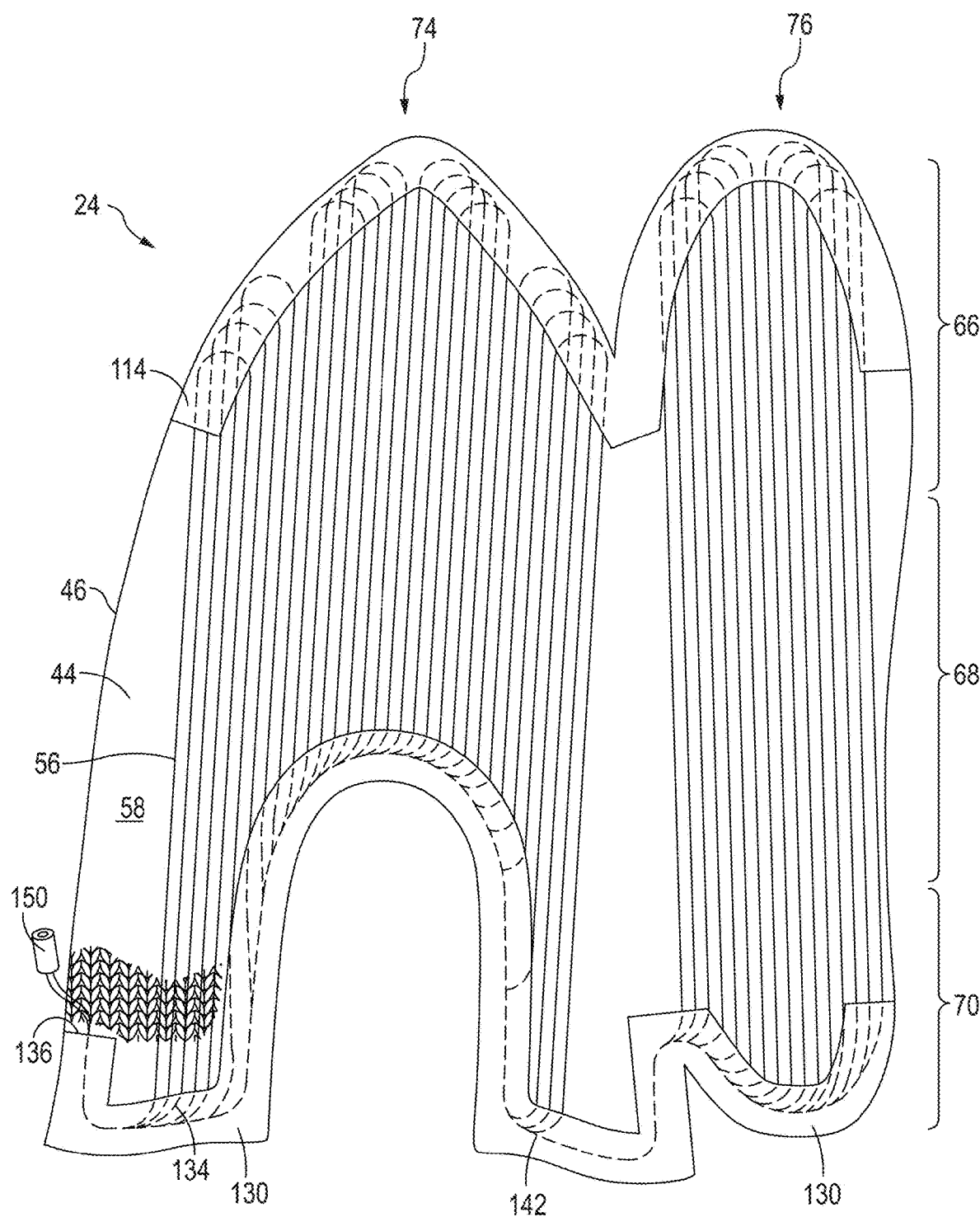
FIG. 8 is another plan view showing the internal surface of the knit element that forms the upper after having routed optical fibers.
Figure 9:
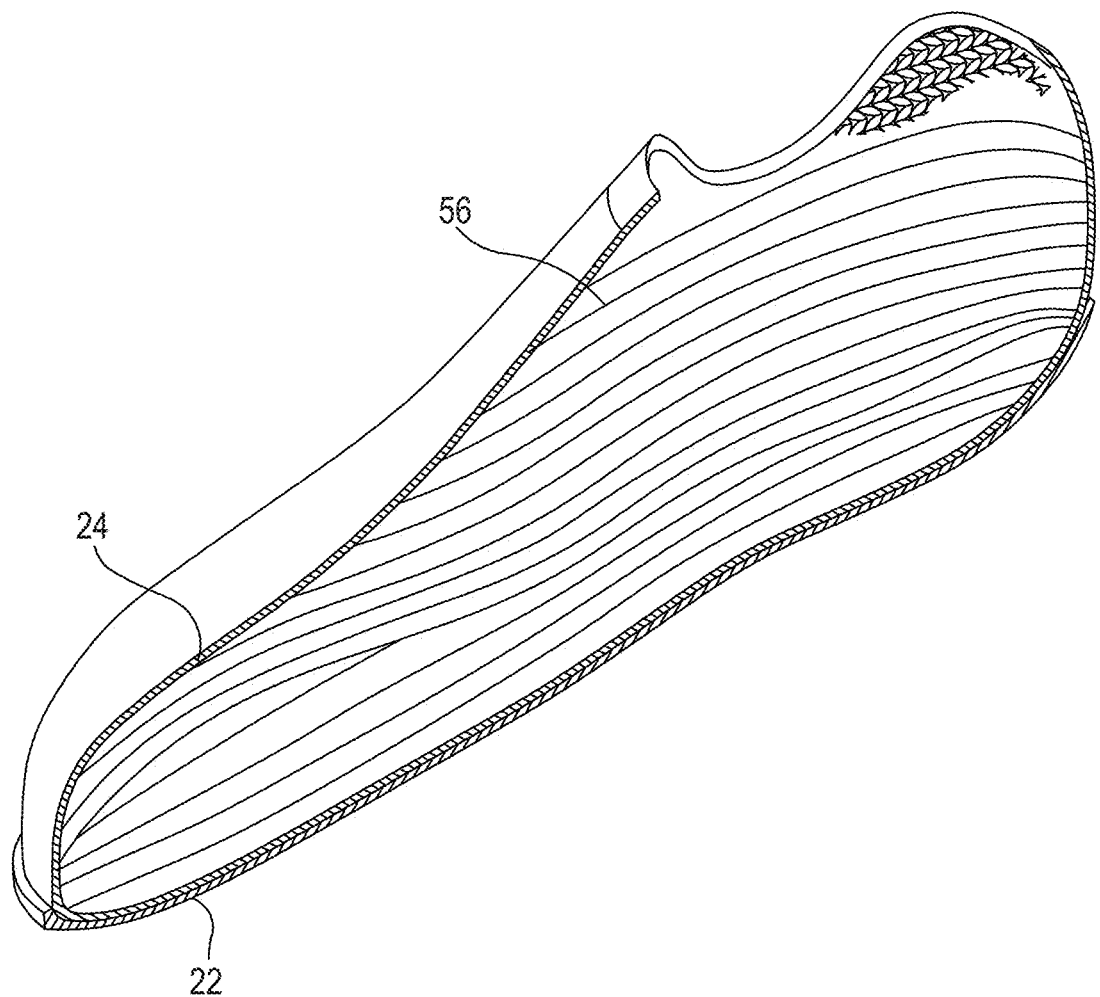
FIG. 9 is a perspective cross-sectional view of the article of footwear shown in FIG. 1A.

With reference to FIG. 8, the heel area 70 includes a double layer construction to define a routing tunnel 130 in the heel area 70. The plurality of optical fibers 86 are routed through the routing tunnel 130 and terminate adjacent the opening 38. The routing tunnel 130 in the illustrated embodiment is provided along the peripheral edge 46 within the heel area 70. One or more entry openings 134 can be provided in the routing tunnel 130 to allow the optical fibers 56 to enter into the routing tunnel 130. The plurality of optical fibers 86 can exit the routing tunnel 130 through an exit opening 136 prior to connecting with the light source 80. The optical fibers 86 when in the routing tunnel 130 are positioned between opposing layers of the double layer construction of the routing tunnel 130. The optical fibers 86 can be bundled within the routing tunnel 130 prior being received in a light source connector 150.

During the knitting process, one optical fiber 56 can be inlaid onto the knit element 44 along spaced courses of the knit element 44 so as to form the respective loops 106a, 106b, 106c and 106d in the forefoot area 66 and respective loops, which are not visible, offset from and beyond the heel area 70. The optical fiber 56 is then cut, preferably at each loop that is offset from and beyond the heel area 70, to provide tails sections 140 and cut ends 142. Each cut end 142 receives light from the light source 80 (see FIG. 10). With regard to the illustrated embodiment, it has been found that allowing light to enter into the optical fibers 56 through both cut ends 142 allows for nearly 200% of the light output as compared to introducing the same amount (energy) of light into only one end of the optical fiber 56. Also with regard to the illustrated embodiment, it was found to limit the length of each optical fiber 56, after the optical fibers 56 are cut, to less than one meter from one cut end 142 to the other. If the optical fibers 56 are longer than one meter, the light output is decreased in sections of the optical fiber 56 farthest from the light source 80.

Figure 10:
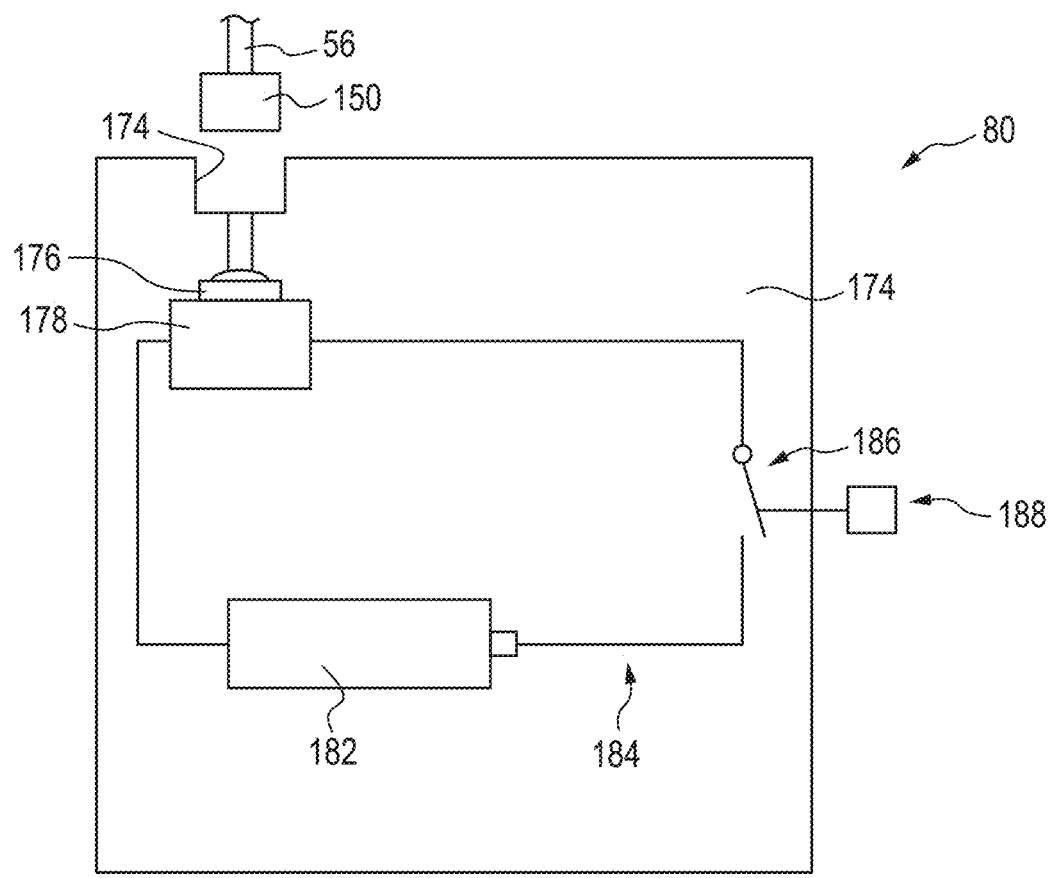
FIG. 10 is a schematic depiction of a light source for use with the footwear.

With reference to FIG. 10, the light source 80 optically connects with each optical fiber 56. The plurality of optical fibers 56 terminate at the light source connector 150 that can be received in a socket 172 provided in an electronics module 174. With the connector 150 received in the socket 172, each end 82 (FIG. 3) of each optical fiber 56 is positioned with respect to the light source 80, which can include a laser diode 176 mounted on a circuit board 178, so that light emanating from laser diode 176 enters the plurality of optical fibers 56. The electronics module 174 can also include a power source 182, such as a battery that can be disposable or rechargeable, electrically connected with the laser diode 176, which could also be an LED or other light source, through a circuit 184 including a switch 186. The switch 186 can be opened and closed using an actuator 188 to control power delivery to the laser diode 176. The laser diode 176 can be one that emits light having a therapeutic wavelength. The laser diode 176 may be configured to project light at wavelengths between 630 nm and 900 nm, or at other wavelengths which also may have a therapeutic effect.

Figure 11:
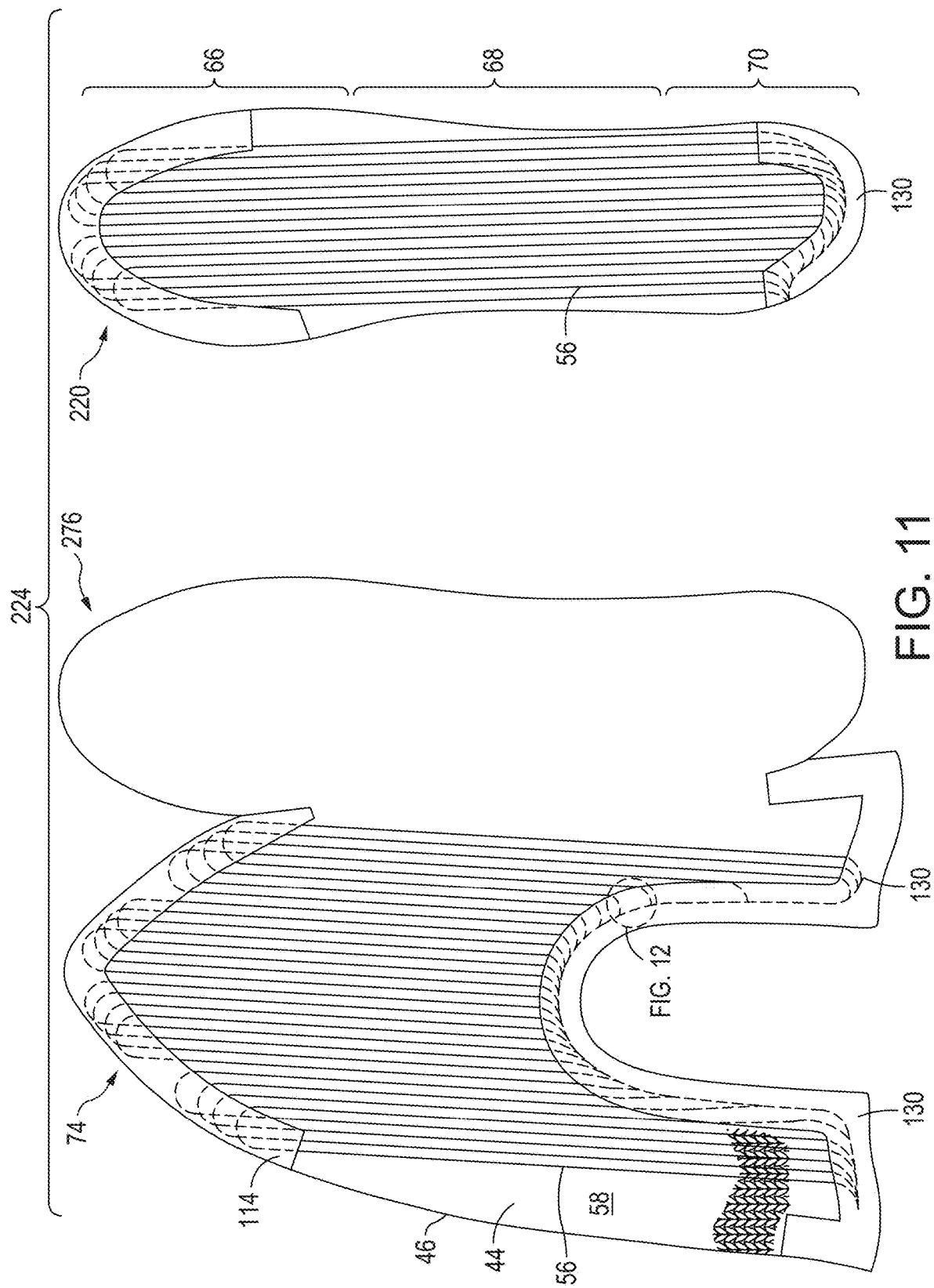
FIG. 11 is a plan view showing an internal surface of an alternative knit element that forms an upper having a separate sock liner.

FIG. 11 depicts an embodiment in which an upper 224 includes an illuminated sock liner 220. The sock liner 220 can be made similar to the knit element 44 described above or can be another fabric element having the optical fibers 56. One difference between the upper 24 depicted in FIG. 8 and the upper depicted in FIG. 11 is that the lower portion 276 of the upper 224 is devoid of optical fibers. This can be beneficial when attaching the sole structure 22. The sole structure 22 can be attached to the lower portion through a process involving high heat, which could damage the optical fibers 56. As such, the top portion 74 and the lower portion 276 can be manufactured, then the sole structure 22 can be attached to the lower portion 276, and then the sock liner 220 can be inserted.

Figure 12:
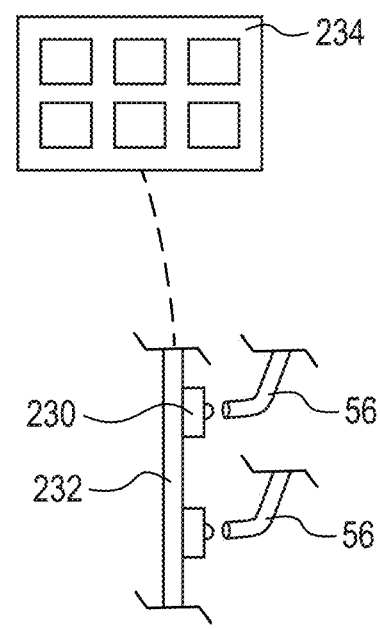
FIG. 12 is a schematic depiction of another light source for use with the footwear.

Another difference between the upper 24 depicted in FIG. 8 and the upper 224 depicted in FIG. 11 is that multiple light sources 230 (FIG. 12) can be provided. The light sources 230 can be LEDs or laser diodes mounted to a flexible circuit 232 that receive power from a power source (for example a solar array 234 depicted in FIG. 12, which could be mounted on the footwear 10). Each light source 230 can be optically connected with a respective optical fiber 56 so as to project light into one end of the respective optical fiber. Each light source 230 and the respective flexible circuit 232 can be located in the routing tunnel 130 so as to be hidden by the double layer construction. The sock liner 220 can be made in a similar fashion.

In the embodiments described above, the uppers 24, 224 can be made in a manner that the exterior surface of the upper is visible when the footwear is being worn, or alternatively, the upper 24, 224 can be covered by a decorative layer. In each instance, however, the optical fibers 56 are positioned so as to project radiation having a therapeutic wavelength through the optical fiber 56 and toward at least one of the wearer's foot, ankle or leg when the footwear 10 is being worn so as to at least partially cover the wearer's foot. Additionally, the light source 80 and the light sources 230 could be controlled to provide selective control as to which areas are being illuminated. For example, only the optical fibers 56 in the bottom portion 76 may be illuminated while those in the top portion 74 are not, if desired.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. An insert for an article of footwear, wherein the insert is a sockliner configured to be inserted into the article of footwear having an internal surface facing the wearer's foot, the insert comprising at least one optical fiber on the internal surface, the at least one optical fiber being configured to project radiation having a therapeutic wavelength through the at least one optical fiber and toward the wearer's foot when the footwear is being worn;
   wherein the at least one optical fiber is at least one side-emitting optical fiber configured to emit light 360 degrees around an axis aligned along a length of the at least one side-emitting optical fiber; and
   wherein each end of the at least one side-emitting optical fiber is received in a light source connector and receives light from the same light source.

2. The insert of claim 1, wherein the at least one side-emitting optical fiber includes at least one optical fiber that crosses over an adjacent optical fiber.

3. The insert of claim 1, wherein the sockliner is a fabric element and the at least one optical fiber is retained to or integrated with the fabric element.

4. The insert of claim 3, wherein the at least one optical fiber provides structural integrity to the fabric element.

5. The insert of claim 3, wherein the at least one optical fiber is configured to accommodate a tensile force applied to the fabric element.

6. The insert of claim 3, wherein the at least one optical fiber is embroidered to the internal surface.

7. The insert of claim 3, wherein the at least one optical fiber is retained to or integrated with the fabric element such that the at least one optical fiber is aligned substantially parallel to a direction of donning of the footwear along at least a majority of a length of the at least one optical fiber when the footwear is being worn.

8. The insert of claim 3, wherein the fabric element is a knit element including a knitted base layer having knitted looped threads that hold in position the at least one optical fiber, which is laid into the knitted base layer during the same knitting cycle as the knitted base layer.

9. The insert of claim 8, wherein the knit element includes a double layer construction to define a fiber-routing tunnel formed during the same knitting cycle as the knitted base layer, wherein the at least one optical fiber is routed through the fiber-routing tunnel.

10. The insert of claim 9, wherein the at least one optical fiber is inlaid onto the knit element to form respective loops; wherein the at least one optical fiber is cut at or adjacent to the respective loops and cut ends of the at least one optical fiber are bundled, inserted through the fiber-routing tunnel and retained by the light source connector.

11. The insert of claim 3, wherein the fabric element is a woven element including a woven threads that are woven with the at least one optical fiber.

12. The insert of claim 1, further comprising a light source.

13. The insert of claim 12, wherein the light source is configured to project light at wavelengths between 630 nm and 900 nm.

14. An insert for an article of footwear, wherein the insert is a sockliner configured to be inserted into the article of footwear having an internal surface facing the wearer's foot, the insert comprising at least one side-emitting optical fiber embroidered to the sockliner, the at least one side-emitting optical fiber being configured to project radiation having a therapeutic wavelength through the at least one optical fiber and toward the wearer's foot when the footwear is being worn;
   wherein each end of the at least one side-emitting optical fiber is received in a light source connector and receives light from a light source.

15. The insert of claim 14, wherein the at least one side-emitting optical fiber is embroidered to the internal surface.

16. An insert for an article of footwear, wherein the insert is a sockliner configured to be inserted into the article of footwear having an internal surface facing the wearer's foot, the insert comprising at least one side-emitting optical fiber affixed to the sockliner, the at least one side-emitting optical fiber being configured to project radiation having a therapeutic wavelength through the at least one optical fiber and toward the wearer's foot when the footwear is being worn, each end of the at least one side-emitting optical fiber receives light from a light source.

17. The insert of claim 16, wherein the at least one side-emitting optical fiber is embroidered to the internal surface.

\* \* \* \* \*